United States Patent [19]

Rosenfeld

[11] Patent Number: 5,170,780
[45] Date of Patent: Dec. 15, 1992

[54] METHOD OF CREDIBILITY ASSESSMENT BASED ON FEEDBACK-ELICITED P3 RESPONSES OF BRAIN

[76] Inventor: J. Peter Rosenfeld, 2526 Hartzell St., Evanston, Ill. 60201

[21] Appl. No.: 707,623

[22] Filed: May 30, 1991

[51] Int. Cl.$^5$ ............................................. A61B 5/04
[52] U.S. Cl. .................................................. 128/731
[58] Field of Search ....................... 128/731, 732, 745

[56] References Cited

U.S. PATENT DOCUMENTS 4,932,416  6/1990  Rosenfeld ........................... 128/731
4,941,477  7/1990  Farwell ............................... 128/731

OTHER PUBLICATIONS

"Feedback-Evoked P3 Responses in Lie Detection", by J. Peter Rosenfeld and G. Todd Bessinger, Northwestern University, published Summer, 1990.
"P300 and Uncertainty Reduction in a Concept-Identification Task", J. H. DeSwart, A. Kok, and E. A. Das-Smaal, Nov. 1981 The Psychophysiological Research, Inc., pp. 619–628, vol. 18 No. 6.
"Event-related brain potentials and subjective probability in a learning task", Richard L. Horst, Ray Johnson, Jr., and Emanuel Dunchin, Memory & Cognition 1980, vol. 8(5), 476–488.

*Primary Examiner*—Max Hindenburg
*Attorney, Agent, or Firm*—Willian Brinks Olds Hofer Gilson & Lione

[57] ABSTRACT

A method for evoking an event related potential in a person in order to evaluate the person's beliefs, knowledge, attitudes, or veracity relating to certain subject matter comprising the steps of presenting the person with a series of statements or questions at least some of which relate to the subject matter, having the person make replies of affirmance or disaffirmance about each statement or question, presenting the person with a purported evaluation of the veracity of each of his replies, each of the evaluations caused to vary to present at least confirmation or disconfirmation of the replies and measuring the P3 of the person in response to the purported evaluations whereby the beliefs, knowledge, attitudes, or veracity of the person about the subject matter can be determined.

17 Claims, 2 Drawing Sheets

FIG. 1

FIG.2A  FIG.2B  FIG.2C  FIG.2D  FIG.2E  FIG.2F ature, a stolen object, or another person's face. Such
METHOD OF CREDIBILITY ASSESSMENT BASED ON FEEDBACK-ELICITED P3 RESPONSES OF BRAIN

BACKGROUND OF THE INVENTION

The present invention relates to a method for evoking, recording and analyzing event-related potentials (ERP), and more particularly to a method of measuring and determining P3 responses from a repeatedly presented stimulus or stimuli interspersed with non-significant stimuli and analyzing the measured ERP responses by means of a computer.

An electroencephalograph (EEG) is a device which measures and records brainwave activity by sensing spontaneous electrical potential of a person's scalp, cortex or cerebrum at various sites. Each EEG channel corresponds to particular electrode combination attached to the subject or patient. The sensed EEG potential at each channel is amplified by a differential amplifier, and the amplifier output signal is typically used to control movement of the recording pen of a polygraph. The EEG record is a long strip of polygraph paper containing a wave form for each EEG channel. The polygraph paper is driven at a predetermined rate (e.g., 30 millimeters per second) and is graduated to represent predetermined time increments. A skilled neurologist must evaluate the EEG record to determine abnormalities in the EEG wave forms.

EEG signals exhibit different frequencies depending upon varying activity. The EEG signal frequencies are classified into four basic frequency bands, which are generally referred to as "Delta" (0.3.5 Hertz); "Theta" (4 to less than 8 Hertz); "Alpha" (8–13 Hertz); and "Beta" greater than 13 Hertz). The neurologist determines the predominant frequency of a particular channel during a particular time period by measuring the period the EEG signal wave form shown on the EEG record. This requires considerable training and is highly dependent upon the skill of the neurologist, since the EEG signal wave form typically includes multiple frequency components.

EEG can be driven by specific extrinsic or endogenous events. For example, a regularly occurring stimulus will elicit a series of waves each time it is presented. The entire series is referred to as an event-related potential (ERP).

Besides the frequency of the EEG or ERP wave forms, the amplitude is often analyzed. Significance has been established when large amplitudes of brain waves occur at about 300 ms or more after the eliciting event. There is evidence to suggest that this P300 wave process is invoked when the updating, or "refreshing", of representations in working memory is required; Donchin, *Psychophysioloqy*, 18, 493–513 (1981); Fabiani, Karis, and Donchin, *Psychophysioloqy*, 22, 588–589 (1985); and others. Large P300's may be elicited by rare or unexpected events, and/or when they are relevant to a task the subject is performing as his brain activity is recorded. Such events may lead to restructuring or updating of working memory, and this activity is part of the ongoing process of maintaining accurate schema of the environment. The updating process may lead to an "activation" of the representation, or to the "marking" of some attribute of the event that was crucial in determining the updating process. This restructuring of the representation of an event is assumed to facilitate the subsequent recall of the event, by providing valuable retrieval cues, so that the greater the restructuring that follows an individual event, the higher the probability of later recalling that event. If P300 amplitude represents the degree of restructuring in working memory, then P300 amplitude should also predict later recall. Fabiani, Karis and Donchin, *Psychophysiology*, Vol. 23, 298–308 (1986).

In view of the current knowledge of the frequency and amplitude of brain wave forms and with the advent of widespread use of the computer in behavioral neuroscience, the analysis of data has become easier.

Oftentimes, it is desirable to have an objective method of determining whether or not a person has seen or otherwise has knowledge of a particular item, such as a weapon, a crime scene configuration, a secrete document, a stolen object, or another person's face. Such knowledge is what is taught by prior art procedures and devices used in "guilty knowledge" tests, a sub-category of procedures used in physiological detection of deception ("lie detection"). The present invention is directed to a reliable, valid easy-to-use and accurate procedure for determining guilty or other knowledge or personal beliefs on the part of an individual whose simple verbal report may be unreliable for various reasons. The present invention also may reveal concealed beliefs, attitudes, or opinions.

If a discreet stimulus, such as a sound, a light flash, or a tap, for example, is presented to a human, his electroencephalogram shows a series of time-locked responses called event related potentials (ERP). It was shown in the 1960's that if a subject is presented with a series of stimuli of two types, e.g., a high tone and a low tone, and if either of those tones is presented in 20 of 100 trials (with the remaining 80 trials containing the other tone), the rare stimulus will evoke a large ERP referred to as "P3" or previously described P300 brain wave. In this so-called "oddball" paradigm, it is known that P3 amplitude varies with rarity. Sutton, S. et al., *Science*, 150, 1187–1188, (1965).

In the 1970's and thereafter, other workers also using an "oddball" paradigm, reported that P3 is evoked by words (or pictures) previously seen by a subject when presented in a word (or picture) series which also includes novel words (or pictures) which fail to evoke P3. Karis, D. et al., *Cognitive Psychology* 16, 177–216; Neville, H. et al., *Proc. Nat. Ac. Sci. U.S.A.*, 79, 2121–2123 (1982).

U.S. Pat. No. 4,932,416 (which is incorporated herein by reference) utilized the "oddball" method for evoking P3 as the basis of a novel set of knowledge detection procedures including guilty knowledge detection, control question testing, and other "lie detection" and related procedures.

SUMMARY OF THE INVENTION

The present invention provides a method and means for evoking an event related potential in a person in order to evaluate the person's knowledge, beliefs, or veracity relating to certain subject matter comprising the steps of presenting the person with a series of statements or questions at least some of which relate to the subject matter, having the person make replies of affirmance or disaffirmance about each statement or question, presenting the person with a purported evaluation of the veracity of each of his reply statements, each of the evaluations caused to vary to present at least confirmation or disconfirmation of the reply statement, and measuring the P3 of the person in response to the purported evaluations whereby the knowledge, belief, or veracity of the person about the subject matter can be determined.

BRIEF DESCRIPTION OF THE FIGURES

FIG. 2B is another graphical waveform representing an ERP indicating a different reaction to that of FIG. 2a.

DETAILED DESCRIPTION OF THE PRESENTLY PREFERRED EMBODIMENTS

According to an embodiment of the present invention, there is provided a method of evoking the P3 wave for the application of evaluation the veracity and/or credibility of replies of persons. This method will be referred to as the "feedback" paradigm, which proceeds as follows:

(1) A subject is asked a question (or presented with a statement). (2) The subject answers the question, or agrees or disagrees with the statement (and, optionally, states how confident he is in the correctness of his response). (3) The subject is provided with feedback as to whether or not he is correct. (4) It is the subject's physiological ERP response to the feedback which is evaluated to allow inferences about the credibility of the subject's initial credibility regarding his verbal utterance.

This "feedback" method ha been used in the ERP research literature exclusively so as to prove or disprove hypotheses regarding the psychological mediation of the P3 response. Thus, although it was also noted here in this regard that the P3 response was thought to represent an updating process for working memory, it was also thought to represent—indeed related to its updating function—the brain's response to reception of surprisinq information. Thus, two exemplary prior art uses of the feedback paradigm were provided by Horst et al., *Memory and Cognition,* 8, 1980, 476–488 and de-Swart et al., *Psychophysiology,* 18, 1981, 619–629. In the former, subjects were taught a series of paired associate word-pairs. They were then tested for recall by presentation of the first member of the paired associates. After they responded and stated their confidence in their responses, they viewed the correct response on a computer terminal. It was found that surprising feedback—either disconfirmation of a confident but incorrect response, or confirmation of a low confident but correct response—evoked large P3 responses. In the deSwart et al. study, subjects were given a set of mathematical or abstract questions to answer, and again, received feedback following their answers. The results paralleled those of Horst et al.: a disconfirmed confident incorrect response, or a confirmed low-confident correct response produce large P3 ERPs. Non-surprising feedback in both the deSwart et al. and Horst et al. reports failed to evoke large P3 responses. Examples of non-surprising information include confirming feedback to confident, correct responses or disconfirming feedback to low confident, incorrect responses. These results were taken as support for the theoretical notion that disconfirmed expectancy—surprise—provoked P3 genesis.

In an embodiment of the present invention, the method proceeds generally as follows: A subject is connected to an electroencephlegraph for the recording of brain waves. The subject may be asked personal questions concerning his attitudes, thoughts, memories, actions, behavior, etc. Each question appears on a computer terminal screen and the subject repeats the question and then responds "Yes" or "No". The subject has been led to believe or told by the operator-experimenter that a computer will analyze his recorded brain waves as he answers to determine his veracity, and also that the computer will then "respond" by flashing a message on the screen stating "true" or "false" (or "lie" or words to these effects), which the subject must then repeat. In fact, the computer's responses do not depend on any analysis of subject data, but are determined by a pre-existing schedule (which may be systematic or random) built into the computer program so that a certain percent of the subject's answers on a given question will evoke a "true" and the remainder, a "false". The feedback itself is thus false at times and unrelated to the subject's cognitions or emotions at the time of his answer. The computer analysis is in fact primarily directed at analysis of subject's brain ERP responses to the feedback message ("True" or "False").

The above described method is based upon the reasoning that a truthful person telling the truth on a given item will have the expectation of being believed. If his honest verbal response leads to a "false" feedback message from the computer, his consequent surprise and disconfirmed expectancy should result in a large P3 response to the feedback, "false". In contrast, a dishonest person telling a lie on a given item should be less surprised when he receives the feedback "false" and will have smaller P3. Thus, one can discriminate truthful and deceptive responses based on P3 responses to feedback. The same logic applies to subject's responses to "true": An honest verbal response followed by "true" should then be followed by a large P3 in response to "true", but a dishonest response leading to a "true" feedback message should be followed with a large P300 in response to the surprising confirmation of a wrong (untrue) response. Thus the P3 response to "True" as well as to "False" can discriminate honest versus dishonest answers.

In one embodiment of the present invention, there are two kinds of feedback, "Lie" and "*". Subjects were told "*" meant "probably true." "Lie" occurs only in response to relevant question feedback on half the relevant-question trials; "*" occurs on the rest of the relevant trials and all the other question trials. There are three other "control" questions and each question is presented with equal probability, therefore, the probability of feedback "Lie" is 0.125, but the probability of "*" is 0.875. Therefore, having unique physical properties in the context of a "***" series, "Lie" is an oddball, but it is in this sense equivalent for both innocents and guilties who both show oddball-evoked P3s- responses to it. In the described embodiment of the present invention, it is not simply the presence of oddball-evoked P3 which yields diagnosis, it is the relative size: In guilties, it is mostly the oddball effect which elicits P3; innocents, in contrast, have the oddball effect plus the effect of disconfirmed expectancy—the surprise of learning that their honest answers are disbelieved—contributing to P3 amplitude. This is one of the aspects of the present invention that distinguish it from the invention of the '416 patent which utilizes exclusively the oddball effect to yield guilty/innocent diagnosis.

Thus, in the present invention, in contrast to the invention disclosed in U.S. Pat. No. 4,932,416, there is no necessity for a target question that serves the purpose of forcing the subject to attend to the display. In the present invention, the subject verbally repeats questions aloud; this is the attention-forcing method. Another aspect of the present methodology is the long "interstimulus interval" or time interval ( >9.0 sec) between the key P3 eliciting events. This is necessitated by time-consuming features of the present invention's trial structure, such as need for subject repetition of questions and feedback signals (detailed below). By contrast, since the invention described in U.S. Pat. No. 4,932,416 depends on the oddball effect which is known to have an optimal interstimulus interval of less than 5 sec and usually around 2 sec, that invention must use a relatively short interstimulus interval, e.g. <3 sec.

The technical procedures for recording and analyzing P3 waves are similar to those previously disclosed (Rosenfeld et al., "An ERP-based, control-question lie detector analog, etc." *Psychophysiology* (in press), and in U.S. Pat. No. 4,932,416 and U.S. Ser. Nos. 537,319 and 495,284, which are a continuation and a CIP, respectively, of U.S. Pat. No. 4,932,416. The disclosures of each of these documents are specifically incorporated herein by reference. The technical procedures for recording P3 waves are briefly described in reference to FIG. 1 as follows:

RECORDING PROCEDURES

Figure 1:
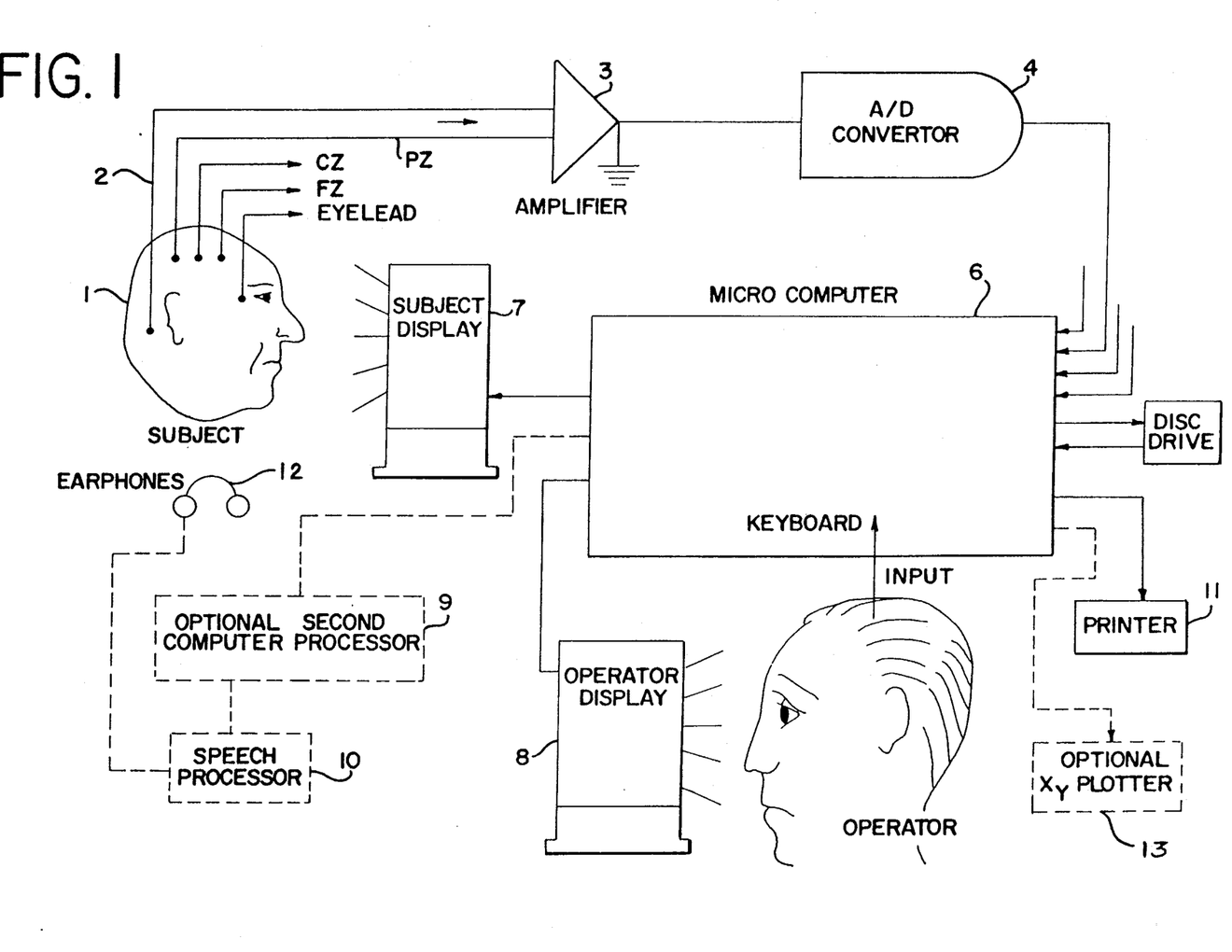
FIG. 1 is a schematic representation of the system utilized in the present invention for P300 analysis.

Silver cup electrodes 2 are placed on Fz, Cz and Pz scalp loci 1, and referenced to linked mastoids with the forehead grounded. Electrodes are also placed supra- and sub-orbitally for EOG recording. Signals are amplified 375,000 times by Grass P511-K preamplifiers with 3 db filters set to pass signals between 0.3 and 30 Hz. As will be described, for display purposes off-line digital filtering is done with some waveforms so that the 3 db upper cut-off is reduced to 2.89 Hz (grand averages), 4.23 Hz (individual averages), or 6.11 Hz (single sweeps). Conditioned signals are then lead to an 8-bit analog-to-digital converter 4 (such as Computer Continuum, Inc., Daly City, Calif.) interfaced to a personal computer and sampled about every 8 msec (rate =125 Hz). Recording begins 104 msec prior to stimulus presentation and ends 2.048 sec later.

STIMULUS PRESENTATION

A table of at least 324 randomly selected numbers between 1 and 8 is stored in the computer program and referred to on each trial by the program so as to determine which of the questions or stimulus phrases is to be presented to the subject on that trial. The numbers were previously generated off-line by a random-number generating program and placed into a table as they were generated, subject to the restriction that no two consecutive trials could contain the same number (stimulus phrase). Trials containing EOG (eye movement) artifacts (signals >40 mV) are rejected (i.e., all data erased) and replaced with the next trial number in the quasi-random table. Typically, trials are generated until about 108 are collected. Thus there are at least 13 trials intended for each of 8 stimuli. Because of artifact replacements and consequent departures from the stored table's original order, the actual range of numbers of trials averaged for each phrase varies.

The numbers/parameters and commercial brand names just given are exemplary but not absolute. If, for example, a different A/D converter (such as a 12 bit model) is selected (and it can be) the amplification could be 100,000 (vs. 75,000).

TESTING PROCEDURE

The procedure for running a subject through the paradigm have many possible variations in terms of the structure and number of the set of questions used in the actual test. What will be now described is one specific variation which has been used and described in a laboratory analog of a "lie-detector" test; (see Rosenfeld, J.P. and Bessinger, G.T. "Feedback-evoked P3 responses in lie detection", *Psychophysiology Supplement*, Vol. 27, Number 4A, August, 1990, page 560, specifically incorporated herein by reference).

In that study, subjects entered the lab and were immediately asked to fill out the consent form. They were then told that due to the nature of the experiment, they would be asked to answer questions about some possibly antisocial or illegal acts. They were told that they would reply to these questions on a questionnaire after the experimenter had left the room and that their responses would remain anonymous. Subjects were also told that they could tear up the questionnaire after the experiment if they wished. If subjects chose to continue the experiment, the experimenter attached the electrodes while explaining how traditional polygraphy works and the older polygraph's inadequacies. In addition, the experimenter gave the subject basic background information on the P3 lie detector (i.e., why the inventor began researching lie detectors, how some other P3-based lie detector paradigms worked, etc.).

After attaching the electrodes, the experimenter initiated playing a tape explaining each question on the questionnaire and left the room. Each subject then listened to the tape recording by himself while filling out the questionnaire. Unbeknownst to the subject, the experimenter observed the subject filling out the questionnaire via a closed circuit video monitor in the next room. The questionnaire had 13 items with "yes" and "no" boxes next to each item. The subject would honestly check "yes" or "no" believing himself to be in secrecy. The subjects were then led into a room with a recliner and recording equipment; electrodes were applied while the experimenter explained how our laboratory became interested in detection of deception. The aim of this explanation was to impart a serious attitude. Next the experimenter gave the subject a list of 13 acts, which check boxes next to each:

1. "SMOKED POT MONTHLY", 2. "STOLEN A BICYCLE", 3. "CHEATED DURING TEST", 4. "TOOK SCHOOL RECORDS", 5. "USED FALSE MEDICAL", 6. "STOLE AN AUTOMOBILE", 7. "FAILED ONE COURSE", 8. "STOLE SOME CLOTHES", 9. "PLAGIARIZED A PAPER", 10. "WAS COMPUTER CHEAT", 11. "TOOK

FRIEND'S MONEY", 12. "USED FALSIFIED I.D.", 13. "BROKEN POP MACHINE."

When the experimenter gave each subject the list, he informed the subject that he would leave the room and shut the door, following which the subject was to turn on a cassette recorder and listen to the loaded tape which would detail the meanings of the listed acts, as well as instruct the subject about checking "yes" or "no" boxes next to each item. Possibly ambiguous items (e.g., "Used False Medical") were explained (e.g., "Used False Medical" means presenting a forged medical note to avoid an exam or term paper deadline") in the tape. All items were defined with respect to a five year period dating back from the date of the subject's present appearance in the lab. Subjects were instructed on the tape to check "yes" or "no" only when they were certain; otherwise they were to write a question mark. Subjects were told that the point of this list filling was to help them clarify in their own minds what acts they were and were not guilty of, and that they could destroy or retain their lists after completion.

While some of the listed items (1,3,5, 7,9,10,11,12,13) were known from pilot studies to have actual probabilities of 10-50% and others were known to have probabilities <2% 2,4,6,8) in the subject student population, all items were estimated by subjects to have similar, finite (Mean=22.7%) probabilities, i.e., to represent acts that one might reasonably suspect at least some members of the subject population to have been involved in at one time or another. The aim in development of this list was to make it likely that most subjects would be guilty of 0-3 items. This would make it possible, in the main control question test analog to come later, to present guilty subjects with a set of items of which only one was a guilty item, and to present innocent subjects with a set of all innocent items. Subjects guilty of too many acts from the original list could not be run since such sets could not be developed with these subjects. The experimenter's knowledge of guilt or innocence on the listed items was thus essential not only as ground truth to validate the ERP test results, but also to arrange for the appropriate item sets to be given to guilty and innocent subjects.

This knowledge was obtained by secret television surveillance of each subject's list as he checked a "yes" or "no" box next to each listed act. Later debriefing revealed (based on subjects' verbal reports) that all but one of the subjects believed themselves to be unobserved and alone while checking the list boxes. (The exceptional subject's data was not used.) Moreover in an unpublished pilot study with similar methods, one final, nine-item questionnaire was given at the end of the study (but prior to any debriefing) to this other sample of 30 subjects from the same population. There was only one item of real interest to us on this questionnaire: "I am comfortable that my privacy was respected in this study." (The preceding four and subsequent items related to subjects' physical comfort, understanding of instructions, experimenter courtesy, etc.) All subjects but two checked "4" or "5" on a 1-5 scale of agreement; the two exceptions checked "3". Thus although it was true that, as told to the subjects, the list-filling was intended to make clear in their own minds what their guilty acts were, it was also true (and not clearly told to subjects) that observations would be made their lists so as i) to arrange stimulus sets, and ii) to ascertain a validating "ground truth" record. When the subject completed the questionnaire, he called for the experimenter who re-entered the room.

Each subject was then told that he would be asked four questions, one-at-a-time from his questionnaire, and that the wording of the questions would vary but the meaning would be clear (e.g., "Are you a monthly pot smoker?" and "Do you smoke pot monthly?"). The subject was instructed to answer each question aloud as if he was innocent of all the items, e.g., "No, I do not smoke pot monthly". Therefore, the subject would have to lie to any question of which he was guilty in order to beat the test. In this embodiment, the four questions were selected from among the 13 on the original questionnaire so as to match the a priori probabilities of these 4 in the population of student subjects. Of 24 subjects, 12 were randomly designated (assigned to a) guilty group. Thus, for these subjects one and only one of the 4 items was selected, based on TV surveillance, to be one to which the subject admitted being guilty. For the designated innocent subjects, the secret TV surveillance information was used to ascertain the subject's innocence on four approximately equaprobable acts.

In other embodiments, one would predetermine list structures differently. Norms would be established using standard procedures such as described in the paper "An ERP-based . . . " pp. 29-30, Rosenfeld et al., ., *Psychophysiology*, (in press). After answering the question, the subject was told to avoid blinking. Each subject was told that he would then be given some feedback; if the computer evaluated the subject as being truthful, "***" would be presented on the screen but if the computer evaluated the subject as being a liar, "LIE" would be presented on the screen. The subjects were told to continue to avoid blinking until after the feedback disappeared from the screen. After the feedback disappeared, "BLINK NOW . . . " was presented and the subjects were instructed to repeat the feedback aloud. Subjects were told they could blink until they answered the next question. All questions and "Don't blink" instructions were put from a video terminal the subject watched.

After about 108 artifact-free trials, subjects were debriefed while the electrodes were being removed.

Brainwaves were taken during the presentation of the feedback and the feedback itself was actually predetermined as described based on the subjects' response to the questionnaire.

The time structure of one trial of the main run of the experiment is as follows:

TABLE A

| Question asked, wait 3 sec for subject to repeat aloud question and deny guilt | Screen Blanked | Feedback given with "Don't Blink" instruction; subject repeats feedback aloud | "Blink now" instruction | Next question etc. |
|---|---|---|---|---|
| 3 sec | 1 sec | 2 sec | | 3 sec intertrial interval |
| | Blank screen delay | Brain Waves Recorded | | |

A purpose of having the subject repeat questions and feedback is to be sure he is paying attention to the stimulus display.

The detailed structure of the set of events in this specific application (embodiment) is shown below in Table 1.

TABLE 1

| | Col. 1 Question | Cols. 2, 3 Subject's Response* Guilty/Innocent | | Col. 4 Feedback | Col. 5 Trial Type | Col. 6 Probability | Cols. 7, 8 Theoretically Predicted Brain Response to Feedback Innocent Subj./Guilty Subj. | |
|---|---|---|---|---|---|---|---|---|
| #1 | ("relevant") item | False | True | LIE | a | .125 | (i) Big P3 | (ii) Small P3 |
| #1 | ("relevant") item | False | True | *** | b | .125 | (iii) No P3 | (iv) Small P3 |
| #2 | ("control") item | True | True | *** | c | .125 | No P3 | No P3 |
| #2 | ("control") item | True | True | *** | d | .125 | No P3 | No P3 |
| #3 | ("control") item | True | True | *** | e | .125 | No P3 | No P3 |
| #3 | ("control") item | True | True | *** | f | .125 | No P3 | No P3 |
| #4 | ("control") item | True | True | *** | g | .125 | No P3 | No P3 |
| #4 | ("control") item | True | True | *** | h | .125 | No P3 | No P3 |

*All subjects say "no" all the time. Only guilty subjects are lying on item #1.

It is seen in Table 1 that each of items (#2,3,4) is always followed by the true feedback which is "*", and that the key item of interest (a guilty item for guilty subjects and a randomly selected innocent item for innocent subjects) is followed by "*" half the time and "LIE" the remaining times. The predictions shown in the last two columns are based on the expected disconfirmed expectancy in innocent (i) subjects (being told "LIE" when they are confidently truthful) and guilty subjects (iv) being told "*" when they knowingly lie. The small P3 shown as predicted outcome (ii) is expected on the basis of the oddball effect; i.e., "LIE" is physically a rare stimulus 0.125 probability) among "*" stimuli 0.875 probability).

Figure 2A:
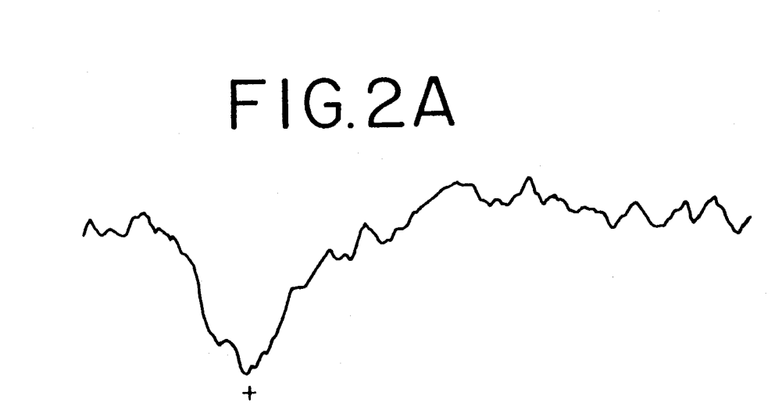
FIG. 2A is a graphical waveform representing an ERP (event related potential) measured in connection with the practicing of an embodiment of the invention described herein and which may be conducted with the equipment depicted in FIG. 1.
Figure 2B:
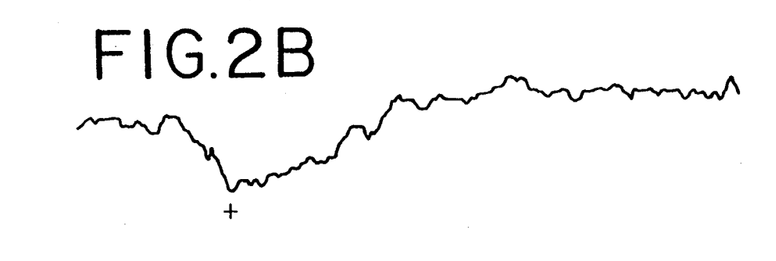
Figure 2C:
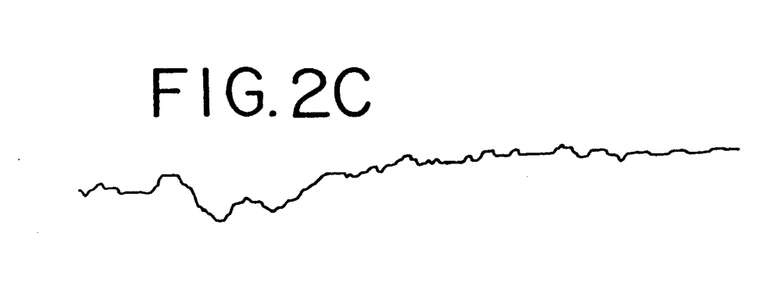
FIG. 2C is another graphical waveform representing an ERP indicating another reaction.
Figure 2D:
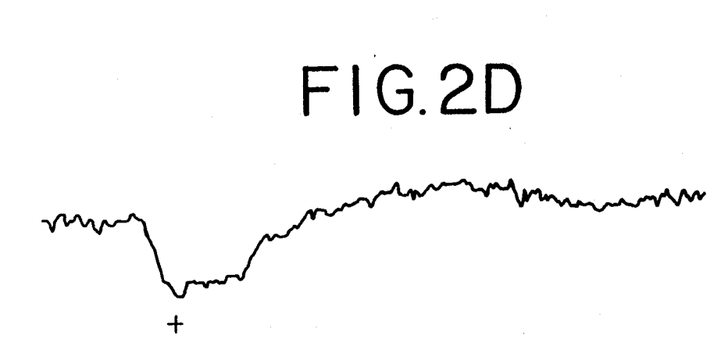
FIG. 2D is another graphical waveform representing an ERP indicating another reaction.
Figure 2E:
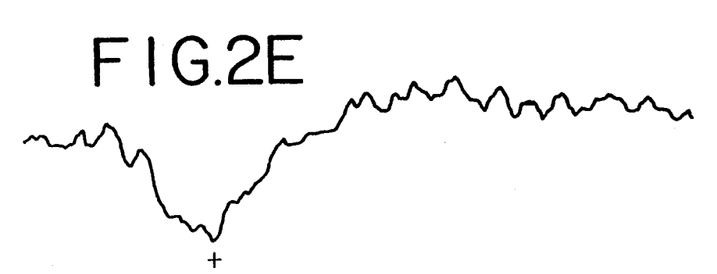
FIG. 2E is another graphical waveform representing an ERP indicating another reaction.
Figure 2F:
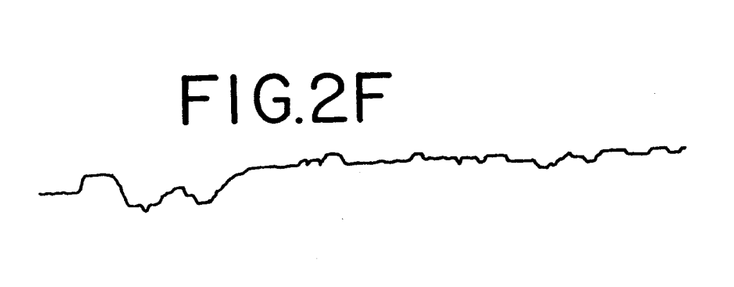
FIG. 2F is another graphical waveform representing an ERP indicating another reaction.

In the publication (Rosenfeld & Bessinger, 1990) the key prediction was that the P3 response at Pz to "LIE" would be bigger in innocents than in guilty subjects. This was confirmed in a t-test (t(22)=3.518, p<0.01). This was a test of group means. In the field, individual data would need to be evaluated. There are many standard ways (published) in which this could be done: (1) Norms for guilty and innocent subjects could be determined for responses to "LIE" and fiducial criteria can be determined. (2) Comparison can be made between trial types a and b (see Table 1, Column 5). The expected value of (a−b) in guilties is >0, in innocents is <0. Such comparisons can be made as described in Rosenfeld et al. (in press), Wasserman and Bockenholt ("Bootstrapping", *Psychophysiology*, 26, 208-221, 1989), and J.J. Allen and W.G. Iacono ("An intra-individual method of analyzing the late positive components of event related potentials" in *Psychophysiology Supplement*, Vol. 27, Number 4A, August, 1990, p. 514). Referring to FIGS. 2A-2F, these are ERP's evoked by feedback in experiments by Rosenfeld and Bessinger described in the above text. In FIG. 2A is shown a large P3 evoked by the feedback "LIE" in response to an innocent person's honest denial of guild on a relevant question. In FIG. 2D is shown the much smaller response of a guilty person's response on the same item to the same feedback. In FIG. 2B is shown the response to "TRUE" by an innocent person which is smaller than the response of a guilty person seen in FIG. 2E. In FIGS. 2C and 2F are missing P3 responses of both innocent (FIG. 2C) and guilty (FIG. 2F) persons to the "***" feedback in the same experiments. P3's are shown with arrows.

It is noted that in the embodiment just described, reference is made to "innocent" and "guilty" persons. More generally, the types of individuals discriminable by this method could be "honest" versus "dishonest" or "certain" versus "uncertain", with respect to answers given about opinions attitudes, beliefs, evaluations as well as about their actual acts.

Also, there are many possible variants on the structure shown in Table 1. For example (and as already noted) instead of embedding occasional "LIE" among "*" stimuli, one could embed "TRUE" among more frequent "*" stimuli, with the latter defined to be "probably false." The predictions about relative P3 sizes between, for example, guilties and innocents would now be reversed. One may actually give both embodiments to one subject as a test battery. Most recently, these two embodiments have been combined in a single version that embeds "LIE" and "TRUE" among "*" stimuli. The subject is told that "TRUE" and "LIE" have face value (i.e., mean "true" and "lie", respectively) and that "*" means "computer uncertain." This method is presented below in Table 2a. In preliminary testing, it and its derivatives (Tables 2b-2e) are the most powerful working versions we now have with respect to intra-individual diagnosis. (Note; the symbolism in Table 2a is explained in Table 2 which is a reworking of Table 1, above.)

An alternative procedure is to present "LIE" 50% of the time on item #3 (innocent control item for all subjects, i.e., either innocent or guilty of item #1) in addition to presenting "LIE" 50% of the time on item #1. Therefore, in this manner even a guilty subject is innocent of this #3 item, so that each subject could provide his own control comparison data.

This method, referred to herein as the "S90", provides two clear results, one predicted, and another not predicted: The predicted result was that the P3 difference between the response to "Lie" in item #3 and to "Lie" in item #1 was greater in the guilty than in the innocent subjects. Not expected, however, was that in contrast to results of Rosenfeld and Bessinger (1990), using the method of Table 1, the S90 method resulted in guilty subjects having larger P3 responses in item #3 than did innocent subjects in item #3. (Likewise for item #1, but here the effect was not as clear probably because the feedback effect was acting in opposition for item #1.) The empirical result is that there are, in the S90 method, two indexes allowing discrimination of guilty versus innocent subjects: (1) the familiar (item 3-item 1) P3difference, guilty versus innocent, and (2) the unexpected P3 to item 3 superiority of guilty to innocent subjects. Thus the more powerful discrimination index would be $(KP3_3 - P3_1)$, where $P3_i$ is the P3 in response to "LIE" on item i, and K is a multiplier coefficient $>1$ and of a value to be empirically tuned in future research.

There are a variety of variations on Table 1 which are possible and will be now discussed. It will however first be useful to 1) clarify a methodological detail and its expected empirical consequences, and 2) develop a shorthand, more symbolic form of Table 1 which is more amenable to paradigm comparison. These two matters are now addressed:

1) It was noted above (see Table 1) that the subject in these studies is required to repeat the feedback so as to focus his attention on it. In early embodiments of the invention (such as Rosenfeld & Bessinger, 1990), upon seeing the "Lie" feedback, subjects would simply repeat "Lie." Alternatively, they'd say "star" upon seeing the "*" feedback. Not emphasized before was the expectation that in addition to seeing a smaller P3 to "Lie" in guilty subjects than in innocent subjects, we also expected to see a P3 in response to "*" in the guilty but not innocent subjects (Table 1) when a relevant question was asked. This is because when the relevant question is given, the guilty subject may expect to see a "Lie" feedback but not a "*" feedback since he is guilty. The disconfirmed expectancy is expected to evoke the P3. However, an innocent subject knows he is innocent of the relevant question so the "*" is simply what is expected and should not evoke a bigger P3 than the other "***" feedbacks following other control questions of which both innocent and guilty parties are innocent. Had this expectation been confirmed, the test would be even stronger because another set of measures would be available.

As noted, the early findings confirmed expectations about the LIE-evoked ERP's, but not the *-evoked responses on the relevant items. Here, innocent and guilty subjects alike had small-to-absent P3 responses of equal amplitude. There may be two probable reasons why this occurred: First, not enough attention to "*" was paid, particularly by guilty subjects on the relevant item; i.e., simply repeating "*" was not adequate to force the guilty subjects to thoroughly review in their minds the implication of the feedback, that is, they satiated and perhaps became bored and unfocused. Second, the innocent subject could be responding slightly with a P3 to "*" following a relevant question because this question is uniquely the one which the computer "thinks" evokes a Lie-response as it falsely accuses him of a "LIE" on this item. The "***" picks up oddball quality by association and generalization.

A simple new method for overcoming these obstacles is to require subjects to repeat not only "LIE" or "STAR" but to answer in a complete sentence specific to the question just asked, such as "LIE, the computer thinks I do smoke pot monthly," or "Star, the computer believes I do not smoke pot monthly." In the alternative paradigms (embodiments) to be noted below, this method is utilized and key predictions will also involve differential responses "***" on relevant trials by guilty and innocent subjects.

Table 2 below is derived from Table 1. The symbolism is explained in the legend under the Table 2. The same symbolism is used in subsequent Tables (2a-11), each of which shows an alternative paradigm-structure for the invention, and under each of which is a set of explanatory remarks about the paradigm.

Or one could use one of the following feedback sets in place of Col. 4 in Table 1:

|   | Set 1 | Set 2 |
|---|-------|-------|
| 1) | LIE   | LIE   |
| 2) | *     | LIE   |
| 3) | TRUE  | *     |
| 4) | !     | *     |
| 5) | OK    | !     |
| 6) | +     | !     |
| 7) | GOOD  | +     |
| 8) | +     | +     |

These sets reduce oddball effects by reducing probabilities of the same physical stimuli with implied "true" feedback meanings as would be pre-determined for subjects. One can also alter the probabilities of the various trial types to change the influence of the oddball effect as necessary. Reducing numbers of trials per category averaged, could reduce habituation effects. Dropping the first 1-3 ERPs from the average could reduce generalized arousal influences.

There are several alternative variations or embodiments that may be employed for practicing the invention, but the feedback effect is common to all candidate methods. As suggested above, it may also prove productive to give a set (battery) of these feedback procedures. Also, it may turn out that ERP responses to the questions asked, (i.e., relevant and control) could be also revealing in view of the feedback manipulation.

TABLE 2

| K1.2.3 | K4 = f | K6 = p | K7 = q | K8 = i | K9 = d |
|--------|--------|--------|--------|--------|--------|
| $R1_{gf/it}$ | L | .125 | + | ++ | + |
| $R1_{gf/it}$ | * | .125 | ++ | + | + |
| $C1_{t/t}$ | * | .125 | − | − | 0 |
| $C1_{t/t}$ | * | .125 | − | − | 0 |
| $C2_{t/t}$ | * | .125 | − | − | 0 |
| $C2_{t/t}$ | * | .125 | − | − | 0 |
| $C3_{t/t}$ | * | .125 | − | − | 0 |
| $C3_{t/t}$ | * | .125 | − | − | 0 |

Key

"K1, K2 . . ." are "Column 1, Column 2, etc."
"f" = "feedback".
"p" = "probability".
"g" = "Guilty Subject"
"i" = "Innocent Subject. Column 5 not used.
"$R1_{gf/it}$" = Relevant question number 1 to which a guilty subject responds falsely, to which an innocent subject responds truly; i.e. when both deny guilt.
"$C1_{t/t}$" = Control question number 1 to which all subjects are innocent and respond truly.
"$C1_{f/f}$" = A control question (not in area of real investigation) of which all subjects are guilty and to which all respond falsely.
"L" = "Lie; "*" = "***"
"++" = Large P3, "+" = small P3; "−" = no P3 expected.
"K9" = "d" is the last, most important column since it's a new designation and it shows which innocent versus quilty comparisons will yield key diagnostic outcomes where "++" means strong discrimination of g and i subjects, "+" means less strong discrimination and "0" = no discrimination. Thus the d columns are set off from the others.

TABLE 2a

| k1.2.3 | f | p | g | i | d |
|--------|---|---|---|---|---|
| $R1_{gf/it}$ | L | .083 | + | ++ | + |
| $R1_{fg/it}$ | T | .083 | ++ | + | + |
| $R1_{fg/it}$ | * | .083 | + | + | 0 |
| $C1_{t/t}$ | * | .24 | − | − | 0 |
| $C2_{t/t}$ | * | .24 | − | − | 0 |
| $C3_{t/t}$ | * | .24 | − | − | 0 |

In this table (2a), "T" is a new symbol and means "True", "*" is defined as "computer uncertain." Here, as discussed above in text, the guilty (g) and innocent (i) subjects respond differently to "LIE" and also differently but oppositely to "TRUE". In comparison with Table 1 (same as Table 2), the original Rosenfeld and Bessinger (1990) study, both oddball effects of L and T add to feedback effects here. Advantages: within 1 test, there are 2 differential unique responses guaranteed in each subject.

TABLE 2b

| k1,2,3 | f | p | g | i | d |
|---|---|---|---|---|---|
| R1$_{gf/it}$ | L | .042 | + | ++ | + |
| R1$_{gf/it}$ | T | .042 | ++ | + | + |
| R1$_{gf/it}$ | * | .041 | + | + | 0 |
| C1$_{t/t}$ | * | .125 | − | − | 0 |
| C2$_{t/t}$ | * | .125 | − | − | 0 |
| C3$_{t/t}$ | * | .125 | − | − | 0 |
| C4$_{t/t}$ | * | .125 | − | − | 0 |
| C5$_{t/t}$ | * | .125 | − | − | 0 |
| C6$_{t/t}$ | * | .125 | − | − | 0 |

In this structure, more control questions are used to maintain interest. It is otherwise like Table 2a.

TABLE 2c

| k1,2,3 | f | p | g | i | d |
|---|---|---|---|---|---|
| R1$_{gf/it}$ | L | .083 | + | ++ | + |
| R1$_{gf/it}$ | T | .083 | ++ | + | + |
| R1$_{gf/it}$ | * | .083 | + | + | 0 |
| C1$_{t/t}$ | T | .125 | − | − | 0 |
| C1$_{t/t}$ | * | .125 | − | − | 0 |
| C2$_{t/t}$ | T | .125 | − | − | 0 |
| C2$_{t/t}$ | * | .125 | − | − | 0 |
| C3$_{t/t}$ | T | .125 | − | − | 0 |
| C3$_{t/t}$ | * | .125 | − | − | 0 |

In this structure, in comparison with Table 2a, the "T" feedback is used with control questions to enhance credibility. Some of the oddball effects, however, will then be lose. Table 2d (next) solves this possible problem.

TABLE 2d

| k1,2,3 | f | p | g | i | d |
|---|---|---|---|---|---|
| R1$_{gf/it}$ | L | .083 | + | ++ | + |
| R1$_{gf/it}$ | T | .083 | ++ | + | + |
| R1$_{gf/it}$ | * | .083 | + | + | 0 |
| C1$_{t/t}$ | T | .042 | − | − | 0 |
| C1$_{t/t}$ | * | .083 | − | − | 0 |
| C2$_{t/t}$ | T | .042 | − | − | 0 |
| C2$_{t/t}$ | * | .083 | − | − | 0 |
| C3$_{t/t}$ | T | .042 | − | − | 0 |
| C3$_{t/t}$ | * | .083 | − | − | 0 |

This is exactly like Table 2c except for the p column where the relative ratios of "T" and "*" probabilities are changed.

TABLE 2e

| k1,2,3 | f | p | g | i | d |
|---|---|---|---|---|---|
| R1$_{gf/it}$ | L | .083 | + | ++ | + |
| R1$_{gf/it}$ | T | .083 | ++ | + | + |
| R1$_{gf/it}$ | * | .083 | + | + | 0 |
| C1$_{t/t}$ | T | .125 | − | − | 0 |
| C1$_{t/t}$ | * | .125 | − | − | 0 |
| C2$_{t/t}$ | T | .125 | − | − | 0 |
| C2$_{t/t}$ | * | .125 | − | − | 0 |
| C3$_{f/f}$ | L | .083 | ++ | ++ | 0 |
| C3$_{f/f}$ | * | .083 | + | + | 0 |
| C3$_{f/f}$ | * | .083 | + | + | 0 |

Note here that C3$_{f/f}$ is used and receives an "L" or a "*" feedback. This is a known guilty item (but not in the area of investigation: it's a control not relevant question) or a typical general control question of a broad nature to which all subjects are probably guilty, such as "Did you ever Lie?". All subjects must respond dishonestly to this type of item and when they then get an occasional "L", the test's credibility is enhanced. Otherwise this structure is like that in Table 2c with the latter's advantages. It is of course possible to change the relative "T" and "*" probabilities here so as to derive a version of this structure on the order of that in Table 2d. One could also have 6 rather than 3 control items (e.g., compare tables 2b and 2a). Note: in all these tables (2a-2e), the total probabilities sum to 0.96 rather than 1.0. This is because they were rounded to 3 decimal places. Adding about 0.0005 to each will yield 100%.

TABLE 3

| K123 | f | p | g | i | d | comments |
|---|---|---|---|---|---|---|
| R1$_{gf/it}$ | * | .125 | ++ | − | ++ | |
| R1$_{gf/it}$ | * | .125 | ++ | − | ++ | |
| C1$_{t/t}$ | L | .125 | ++ | ++ | 0 | physical oddball = "po" |
| C1$_{t/t}$ | * | .125 | + | + | 0 | generalization = "gn" |
| C2$_{t/t}$ | * | .125 | − | − | 0 | |
| C2$_{t/t}$ | * | .125 | − | − | 0 | |
| C3$_{t/t}$ | * | .125 | − | − | 0 | |
| C3$_{t/t}$ | * | .125 | − | − | 0 | |

In this structure, one relevant (RQ) and 3 control (CQ) questions are used as in FIG. 2 (Table 1). The innocent cannot discriminate this structure from that of Table 3 (FIG. 2); he doesn't know what the RQ is, he knows only he is falsely accused of one of 3 items of which he is innocent. Advantages: No innocent response to R1$_{gf/it}$ by generalization, and therefore stronger discrimination; i.e., d = ++ (vs + in FIG. 2). Disadvantage: As g-subject is repeatedly missed and all subjects are consistently misaccused 50% of the time, there could be a drop in seriousness with which procedure is taken as time passes. A possible solution: Give occasional "L" to R1$_{gf/it}$. The I subject should assume it is a computer error, the g subject could be more suggestible. Alternatively, give an occasional "no decision" feedback.

TABLE 4

| K123 | f | p | g | i | d |
|---|---|---|---|---|---|
| R1$_{gf/it}$ | * | .142 | ++ | − | ++ |
| C1$_{t/t}$ | L | .07 | ++ | ++ | 0 |
| C1$_{t/t}$ | * | .07 | + | + | 0 |
| C2$_{t/t}$ | * | .142 | − | − | 0 |
| C3$_{t/t}$ | * | .142 | − | − | 0 |
| C4$_{t/t}$ | * | .142 | − | − | 0 |
| C5$_{t/t}$ | * | .142 | − | − | 0 |
| C6$_{t/t}$ | * | .142 | − | − | 0 |

Table 4 In this structure, one relevant and 6 controls are used. It is like Table 3 in that there can be no generalization from the L item to the relevant item. The obvious difference (from Table 3) is that many more CQs are used here (Advantage) which should better maintain attention.

TABLE 5

| K123 | f | p | g | i | d |
|---|---|---|---|---|---|
| R1$_{gf/it}$ | * | .125 | ++ | − | ++ |
| C1$_{t/t}$ | L | .125 | ++ | ++ | 0 |
| C2$_{t/t}$ | * | .125 | − | − | 0 |
| C3$_{t/t}$ | * | .125 | − | − | 0 |
| C4$_{t/t}$ | * | .125 | − | − | 0 |
| C5$_{t/t}$ | * | .125 | − | − | 0 |

TABLE 5-continued

| K123 | f | p | g | i | d |
|---|---|---|---|---|---|
| $C6_{t/t}$ | * | .125 | — | — | 0 |
| $C7_{t/t}$ | * | .125 | — | — | 0 |

This is also the case with Table 5. The multiple controls (in both Table 4 & 5) also make the "*" to $R1_{gf/it}$ a much rarer, i.e., unexpected oddball/P3-evokinq, event. Disadvantage of both Table 4 & 5: The guilty item is always missed as in Table 3. The advantage of Table 5 relative to Table 4 is that there is yet one more control item in Table 5, which enhances interestingness. The disadvantage of Table 5 is that the same C1 item is consistently (100% of time) falsely accused which may impair impression of seriousness.

TABLE 6

| K123 | f | p | g | i | d |
|---|---|---|---|---|---|
| $R1_{gf/it}$ | * | .125 | ++ | — | ++ |
| $R1_{gf/it}$ | * | .125 | ++ | — | ++ |
| $C1_{f/f}$ | L | .125 | ++ | ++ | 0 |
| $C1_{f/f}$ | * | .125 | +(+) | (+) | 0 |
| $C2_{t/t}$ | * | .125 | — | — | 0 |
| $C2_{t/t}$ | * | .125 | — | — | 0 |
| $C3_{t/t}$ | * | .125 | — | — | 0 |
| $C3_{t/t}$ | * | .125 | — | — | 0 |

TABLE 7

| K123 | f | p | g | i | d |
|---|---|---|---|---|---|
| $R1_{gf/it}$ | * | .142 | ++ | — | ++ |
| $C1_{f/f}$ | L | .07 | ++ | ++ | 0 |
| $C1_{f/f}$ | * | .07 | ++ | ++ | 0 |
| $C2_{t/t}$ | * | .142 | — | — | 0 |
| $C3_{t/t}$ | * | .142 | — | — | 0 |
| $C4_{t/t}$ | * | .142 | — | — | 0 |
| $C5_{t/t}$ | * | .142 | — | — | 0 |
| $C6_{t/t}$ | * | .142 | — | — | 0 |

TABLE 8

| K123 | f | p | g | i | d |
|---|---|---|---|---|---|
| $R1_{gf/it}$ | * | .125 | ++ | — | ++ |
| $C1_{f/f}$ | L | .125 | ++ | ++ | 0 |
| $C2_{t/t}$ | * | .125 | + | + | 0 |
| $C3_{t/t}$ | * | .125 | — | — | 0 |
| $C4_{t/t}$ | * | .125 | — | — | 0 |
| $C5_{t/t}$ | * | .125 | — | — | 0 |
| $C6_{t/t}$ | * | .125 | — | — | 0 |
| $C7_{t/t}$ | * | .125 | — | — | 0 |

These paradigms are related to the previous ones (Tables 3–5) in providing discrimination of g and i subjects based on P3 responses to "***" feedback on item $R1_{gf/it}$. They have some advantages (and disadvantages) of the earlier structures as discussed, but they contain a critical new feature, an area of the special control item $C1_{f/f}$, an item of which all subjects are known to be guilty (but in an area not under real investigatory concern by field lie-detectives). The advantage anticipated is the possibility that all subjects may show more interest (attention) when a test correctly detects at least some of their lies (on item $C1_{f/f}$). A possible disadvantage might be that guilty subjects must be motivated to lie on two items and innocent subjects on item $C1_{f/f}$ which becomes now more like a typical control question in the standard polygraph test (which does not use P3 responses) now in use *(Truth and Deception, 2nd Ed.*, by Reid and Inbau, Williams & Wilkins (1977)). Such procedures require extensive pre-examination interviews as discussed by scholarly reviews. Another possible disadvantage is that multiple guilty items may lessen the impact of any single item. Tables 7 and 8 contain structures designed to reduce this effect.

TABLE 9

| | Modified 590 | | | | |
|---|---|---|---|---|---|
| K123 | f | p | g | i | d |
| $R1_{gf/it}$ | L | .125 | + | ++ | + |
| $R1_{gf/it}$ | * | .125 | ++ | + | + |
| $C1_{f/f}$ | L | .125 | ++ | ++ | 0 |
| $C1_{f/f}$ | * | .125 | + | + | 0 |
| $C2_{t/t}$ | * | .125 | — | — | 0 |
| $C2_{t/t}$ | * | .125 | — | — | 0 |
| $C3_{t/t}$ | * | .125 | — | — | 0 |
| $C3_{t/t}$ | * | .125 | — | — | 0 |

TABLE 10

| | [S90 + Table 6] | | | | |
|---|---|---|---|---|---|
| K123 | f | p | g | i | d |
| $R1_{gf/it}$ | L | .125 | + | ++ | + |
| $C1_{f/f}$ | L | .125 | ++ | + | + |
| $C1_{f/f}$ | * | .125 | ++ | ++ | 0 |
| $C2_{t/t}$ | * | .125 | ++ | ++ | 0 |
| $C3_{t/t}$ | * | .125 | — | — | 0 |
| $C4_{t/t}$ | * | .125 | — | — | 0 |
| $C5_{t/t}$ | * | .125 | — | — | 0 |
| $C6_{t/t}$ | * | .125 | — | — | 0 |

TABLE 11

| | [S90 + Table 7] | | | | |
|---|---|---|---|---|---|
| K123 | f | p | g | i | d |
| $R1_{gf/it}$ | L | .07 | + | ++ | + |
| $C1_{f/f}$ | L | .07 | ++ | ++ | 0 |
| $C2_{t/t}$ | * | .07 | — | — | 0 |
| $C3_{t/t}$ | * | .07 | — | — | 0 |
| $C4_{t/t}$ | * | .142 | — | — | 0 |
| $C5_{t/t}$ | * | .142 | — | — | 0 |
| $C6_{t/t}$ | * | .142 | — | — | 0 |
| $C7_{t/t}$ | * | .142 | — | — | 0 |

Here are yet more possible structural variations which combine features of above noted structures with the advantage of the S90 model (shown in Table 9 by itself), gaining advantages and disadvantages of these structures as discussed above. This set of tables is by no means exhaustive. One could, for example, combine S90 with Table 8 much as Table 9 combines S90 and Table 6. Subsequent empirical tests of each possible structure will reveal the most successful discriminator structure (or set of structures in a test battery).

It is intended that the foregoing detailed description be regarded as illustrative rather than limiting and that it is understood that the following claims including all equivalents are intended to define the scope of the invention.

I claim:

1. A method of evaluating the beliefs, attitudes, or credibility of a subject comprising the steps of:
    (1) asking the subject a question;
    (2) providing the subject with feedback as to whether or not a reply by the subject to said question is correct:
    (3) evaluating the subject's physiological ERP response to the feedback to evaluate the subject's beliefs, attitudes, or credibility regarding his reply.

2. The method of claim 1 further including the step of having the subject provide an assessment of how confident he is in the correctness of his response.

3. A method of evaluation the belief, attitudes, or credibility of a subject comprising the steps of:
(1) asking the subject a series of questions to which the subject provides replies:
(2) providing the subject with feedback with respect to each question of said series of questions as to whether or not the reply by the subject to said question is correct; and
(3) evaluating the subject's physiological ERP response to the feedback to evaluate the subject's beliefs, attitudes, or credibility regarding his replies.

4. A method for evoking an event related potential in a subject relating to an event about which the subject may have knowledge, comprising the steps of:
presenting the subject with a series of statements at least some of which relate to the event about which the subject may have knowledge, and further about which said series of statements the subject is to make reply representations of affirmance or disaffirmance;
presenting the subject with a purported evaluation of the veracity of each of the subject's replies, each of said evaluations caused to vary to present at least confirmation or disconfirmation of said replies of the subject;
measuring the P3 of the subject in response to the purported evaluation; whereby the knowledge of the subject about the event can be determined.

5. The method of claim 4 in which the subject provides a representation of the level of confidence in the correctness of each of his reply representations.

6. The method of claim 4 in which the evaluation is a feedback representation.

7. The method of claim 4 in which the subject is informed that the veracity of each of his reply representations is being made.

8. The method of claim 4 in which said evaluations are made to vary in accordance with a predetermined schedule so that a predetermined percentage of said evaluations of the subject's reply representations related to the event affirm said reply representations and a predetermined percentage of said evaluations of the subject's reply representations related to the event disaffirm said reply representations whereby disaffirmance of the subject's negative representation related to the event is indicative of the subjects lack of knowledge concerning the event.

9. A method for evoking an event related potential in a subject relating to an event about which the subject may have knowledge, comprising the steps of:
asking the subject personal questions to which the subject may reply in either the positive or negative;
leading the subject to believe that his answers will be analyzed to determine his veracity and also that an evaluation of his veracity will be presented to him;
providing the subject with a purported evaluation of his veracity; and
analyzing the subject's P3 brain waves whereby the subject's veracity or personal knowledge with respect to certain questions can be determined based upon a comparison of the P3 response to intentionally presented disconfirming and confirming feedback.

10. The method of claim 9 in which the subject's veracity or personal knowledge with respect to certain questions can be determined based upon the following criteria:
a truthful subject providing a truthful reply to a specific question will have the expectation of being believed so that if evaluating feedback is provided in reply to his honest response indicating untruthfulness, his disconfirmed expectancy should results in a relatively large P3 response;
an untruthful subject providing an untruthful reply to a specific question will have a relatively low expectation of being believed so that if evaluating feedback is provided in reply to his untruthful dishonest response indicating untruthfulness, his confirmed expectancy should results in a relatively smaller P3 response;
a truthful subject providing a truthful reply to a specific question will have the expectation of being believed so that if evaluating feedback is provided in reply to his honest response indicating truthfulness, his confirmed expectancy should result in a relatively small P3 response; and
an untruthful subject providing an untruthful reply to a specific question will have a relatively low expectation of being believed so that if an evaluating feedback indicating is provided in reply to his untruthful response indicating truthfulness, his disconfirmed expectancy should results in a relatively large P3 response.

11. The method of claim 9 in which the personal questions asked of the subject concern attitudes, thoughts, memories, actions, or behavior.

12. The method of claim 9 including the step of presenting the personal questions on a computer terminal screen.

13. The method of claim 9 including the step of having the subject repeat each of the questions and then respond affirmatively or negatively in reply to each question.

14. The method of claim 9 wherein the step of providing the subject with a purported evaluation of his veracity further includes flashing a message on a computer screen.

15. The method of claim 9 including the step of having the subject repeat each purported evaluation of his veracity.

16. The method of claim 15 including the step of having the subject answer in a complete sentence specific to the question asked.

17. The method of claim 9 in which the purported evaluations are determined by a pre-existing schedule so that a certain percent of the subject's answers on a given question will evoke a "true" and the remainder, a "false" whereby the feedback itself is thus false at times and unrelated to the subject's cognitions or emotions at the time of his answer.

* * * * *

UNITED STATES PATENT AND TRADEMARK OFFICE
CERTIFICATE OF CORRECTION

PATENT NO. : 5,170,780
DATED : December 15, 1992
INVENTOR(S) : J. PETER ROSENFELD It is certified that error appears in the above-identified patent and that said Letters Patent is hereby corrected as shown below:

Column 1, line 55, please delete "*Psychophysioloqy*" and substitute therefor --*Psychophysiology*--.

Column 1, line 56, please delete "*Psychophysioloqy*" and substitute therefor --*Psychophysiology*--.

Column 2, line 15, please delete "secrete" and substitute therefor --secret--.

Column 2, line 27, please delete "discreet" and substitute therefor --discrete--.

Column 3, line 16, please delete "2a" and substitute therefor --2A--.

Column 3, line 44, delete "ha" and substitute --has--.

Column 3, line 52, delete "surprisinq" and substitute therefor --surprising--.

Column 4, line 13, delete "electroencephlegraph" and substitute --electroencephalograph--.

Column 5, line 43, after "Cz" please insert --,--.

UNITED STATES PATENT AND TRADEMARK OFFICE
CERTIFICATE OF CORRECTION

PATENT NO. : 5,170,780
DATED : December 15, 1992
INVENTOR(S) : J. PETER ROSENFELD It is certified that error appears in the above-identified patent and that said Letters Patent is hereby corrected as shown below:

Column 5, line 47, delete "375,000" and substitute therefor --75,000--.

Column 5, line 47, after "preamplifiers" insert --3--.

Column 5, line 56, after "computer" insert --6--.

Column 6, line 61, delete "which" and substitute --with--.

Column 7, line 25, before "2,4,6,8)" please insert --(--.

Column 8, line 27, please delete ".,".

Column 9, line 27, before "0.125" please insert --(--.

Column 9, line 28, before "0.875" please insert --(--.

Column 9, line 41, please delete "<" and insert --$\leq$--.

Column 9, line 52, please delete "guild" and substitute --guilt--.

Column 9, line 67, after "opinions" insert --,--.

Column 10, line 32, please delete "Note;" and substitute --Note:--.

Column 10, line 57, delete "P3difference" and substitute --P3 difference--.

Column 12, line 39, after "Subject." insert --"--.

Column 12, line 46, after "Lie" insert --"--.

Column 12, line 50, delete "quilty" and substitute --guilty--.

UNITED STATES PATENT AND TRADEMARK OFFICE
CERTIFICATE OF CORRECTION

PATENT NO. : 5,170,780

DATED : December 15, 1992

INVENTOR(S) : J. PETER ROSENFELD

It is certified that error appears in the above-identified patent and that said Letters Patent is hereby corrected as shown below:

Column 12, TABLE 2a, in the left column, third line, delete "$R1_{fg/u}$" and substitute --$R1_{gf/u}$--.

Column 12, TABLE 2a, in the left column, fourth line, delete "$R1_{fg/u}$" and substitute --$R1_{gf/u}$--.

Column 13, line 37, delete "lose" and substitute --lost--.

Column 14, line 55, delete "Table 4".

Column 15, line 9, delete "P3-evokinq" and substitute --P3-evoking--.

COLUMN 17

Claim 3, line 1, please delete "evaluation" and substitute --evaluating--.

Claim 3, line 4, please delete "replies:" and substitute --replies;--.

Claim 8, line 47, delete "subjects" and substitute --subject's--.

COLUMN 18

Claim 10, line 12, delete "results" and substitute --result--.

Calim 10, line 19, delete "results" and substitute --result--.

UNITED STATES PATENT AND TRADEMARK OFFICE
CERTIFICATE OF CORRECTION

PATENT NO. : 5,170,780
DATED : December 15, 1992
INVENTOR(S) : J. PETER ROSENFELD It is certified that error appears in the above-identified patent and that said Letters Patent is hereby corrected as shown below:

Claim 10, line 32, delete "results" and substitute --result--.

Signed and Sealed this

Ninth Day of August, 199

Attest:

BRUCE LEHMAN

Attesting Officer

Commissioner of Patents and Trademarks